United States Patent
Mooradian et al.

(10) Patent No.: US 7,328,060 B2
(45) Date of Patent: Feb. 5, 2008

(54) CANCER DETECTION AND ADAPTIVE DOSE OPTIMIZATION TREATMENT SYSTEM

(75) Inventors: Gregory C. Mooradian, San Diego, CA (US); Steven Saggese, San Diego, CA (US); Michael D. Tocci, Sandia Park, NM (US); Nora C. Tocci, Sandia Park, NM (US)

(73) Assignee: Science & Engineering Associates, Inc., Albuquerque, NM (US)

( * ) Notice: Subject to any disclaimer, the term of this patent is extended or adjusted under 35 U.S.C. 154(b) by 684 days.

(21) Appl. No.: 10/365,012

(22) Filed: Feb. 12, 2003

(65) Prior Publication Data

US 2003/0153825 A1 Aug. 14, 2003

Related U.S. Application Data

(60) Provisional application No. 60/363,997, filed on Mar. 14, 2002, provisional application No. 60/356,302, filed on Feb. 12, 2002.

(51) Int. Cl.
*A61B 6/00* (2006.01)
(52) U.S. Cl. .................................. 600/476; 600/473
(58) Field of Classification Search ................ 600/407, 600/410, 476, 473
See application file for complete search history.

(56) References Cited

U.S. PATENT DOCUMENTS

| | | | |
|---|---|---|---|
| 4,786,813 A * | 11/1988 | Svanberg et al. | 250/461.1 |
| 4,973,848 A * | 11/1990 | Kolobanov et al. | 250/458.1 |
| 5,115,137 A | 5/1992 | Andersson-Engels et al. | 250/461.2 |
| 5,514,127 A | 5/1996 | Shanks | 606/10 |
| 5,612,540 A | 3/1997 | Richards-Kortum et al. | 250/461.2 |
| 5,623,932 A | 4/1997 | Ramanujam et al. | 128/665 |
| 5,624,437 A | 4/1997 | Freeman et al. | 606/12 |
| 5,735,276 A * | 4/1998 | Lemelson | 600/407 |
| 5,782,770 A | 7/1998 | Mooradian et al. | 600/476 |
| 5,916,461 A * | 6/1999 | Costin et al. | 219/121.68 |
| 5,944,748 A | 8/1999 | Mager et al. | 607/88 |

(Continued)

FOREIGN PATENT DOCUMENTS

EP 0429297 A2 11/1990

(Continued)

OTHER PUBLICATIONS

U.S. Appl. No. 60/356,302 filed Feb. 12, 2002, entitled *Cancer Detection and Adaptive Dose Optimization Treatment System*. Applicant: Michael D. Tocci, et al.

(Continued)

*Primary Examiner*—Eleni Mantis Mercader
*Assistant Examiner*—Jacqueline Cheng
(74) *Attorney, Agent, or Firm*—Burns & Levinson LLP; Jacob N. Erlich; Orlando Lopez

(57) ABSTRACT

The present invention utilizes a series of optical and electronic elements to detect and image cancerous and/or pre-cancerous cells in living tissue. The invention further uses the images thus obtained to adaptively and dynamically shape a treatment light beam so as to maximize the beam's intensity in proportion to the areas with the most cancer or pre-cancer and to minimize the irradiation of normal tissue by the beam.

42 Claims, 9 Drawing Sheets

U.S. PATENT DOCUMENTS

| | | | | |
|---|---|---|---|---|
| 6,008,889 | A | 12/1999 | Zeng et al. | 356/73 |
| 6,069,689 | A | 5/2000 | Zeng et al. | 356/73 |
| 6,128,525 | A | 10/2000 | Zeng et al. | 600/476 |
| 6,135,965 | A | 10/2000 | Tumer et al. | 600/476 |
| 6,186,628 | B1* | 2/2001 | Van de Velde | 351/205 |
| 6,208,749 | B1 | 3/2001 | Gutkowicz-Krusin et al. | 382/128 |
| 6,236,881 | B1 | 5/2001 | Zahler et al. | 600/476 |
| 6,256,530 | B1 | 7/2001 | Wolfe | 600/477 |
| 6,347,244 | B1* | 2/2002 | Dubnack | 600/476 |
| 6,413,267 | B1* | 7/2002 | Dumoulin-White et al. | 607/89 |
| 6,605,083 | B2* | 8/2003 | Clement et al. | 606/17 |
| 2002/0007123 | A1* | 1/2002 | Balas | 600/476 |
| 2002/0169505 | A1* | 11/2002 | Jethmalani et al. | 623/6.56 |

FOREIGN PATENT DOCUMENTS

| | | |
|---|---|---|
| EP | 0604931 A2 | 12/1993 |
| EP | 0880941 A1 | 12/1998 |
| JP | 06063164 A | 3/1994 |
| JP | 2001299941 A | 10/2001 |
| WO | WO 95/03089 | 2/1995 |
| WO | WO 98/41158 | 9/1998 |
| WO | WO 00/71045 A1 | 11/2000 |
| WO | WO 01/83030 A1 | 11/2001 |

OTHER PUBLICATIONS

U.S. Appl. No. 60/363,997 filed Mar. 14, 2002, entitled *Multiple Imaging System and Method for Designing Same.* Applicant: Michael D. Tocci et al.

U.S. Appl. No. 10/187,912 filed Jul. 2, 2002 entitled *Multiple Imaging System.* Applicant: Michael D. Tocci.

* cited by examiner

CANCER DETECTION AND ADAPTIVE DOSE OPTIMIZATION TREATMENT SYSTEM

CROSS REFERENCE TO RELATED APPLICATIONS

This application claims priority of U.S. Provisional Application 60/356,302 filed on Feb. 12, 2002, which is incorporated by reference herein, and of U.S. Provisional Application 60/363,997 filed on Mar. 14, 2002, also incorporated by reference herein.

BACKGROUND

This invention relates to detection and treatment systems for cancer and pre-cancer, and more specifically to a detection and treatment system that first detects cancerous and pre-cancerous tissue in situ, and then dynamically and automatically shapes and re-shapes its photodynamic therapy (PDT) treatment beam during the course of treatment to maximize the effect of the treatment beam while simultaneously minimizing the illumination of surrounding normal tissue.

Analyzing living cells using fluorescence of a dye, which is produced in an interaction between tissue and an injected chemical, is a well-understood method in the field of medical science. In this method of analysis, a chemical is introduced into living tissue, where the chemical is preferentially absorbed into cancerous or pre-cancerous cells. The chemical interacts with the living tissue to produce a dye. The dye is highly fluorescent, meaning that it absorbs a particular wavelength of light, and subsequently emits a longer wavelength of light. For example, a dye might absorb 340 nm light very well, and as a result of absorbing such light, will immediately emit large quantities of light in a band centered at 530 nm. Thus, many methods exist that involve introducing a drug into living tissue (either intravenously or topically), waiting for the drug to be interact with the tissue and produce a dye and to be preferentially absorbed by cancerous and pre-cancerous cells, and then illuminating an area of the tissue with 340 nm (ultraviolet) light, while simultaneously receiving light from the area with a detector that is sensitive only to 530 nm light (using a filter, for example, that allows only 530 nm light to pass through to the detector).

Another method for analyzing living cells involves looking at a series of narrow-wavelength-bands of reflected light from the tissue. In this process, broad-wavelength light (for example, white light spanning the range from 400 nm to 700 nm) is used to illuminate the sample. A high-resolution multispectral imager is then used to image the tissue at several different wavelength bands. With this method, it is possible to find locations where larger-than-normal densities of capillary blood vessels occur. The presence of larger-than-normal densities of capillary blood vessels (along with their shape, in some cases) may indicate the presence of cancerous and/or pre-cancerous cells.

Analyzing living cells using autofluorescence spectroscopy is also well understood in the field of medical science. In the process of autofluorescence no drug is introduced to the living tissue. Light of a particular wavelength is simply introduced to the living tissue, and through the process of autofluorescence, light of a longer wavelength is immediately emitted from the same tissue. Compared to the process of fluorescence of a dye, which is produced in an interaction of tissue with an injected drug (described above), the process of autofluorescence produces a great deal less emitted light. In addition, all living cells will emit light from naturally occurring flurophores within the cells.

Thus, the detection of emitted light, and especially the discrimination between light emitted from normal cells and that emitted from cancerous or pre-cancerous cells, becomes a difficult, two-part problem to solve. First, the fluorescence light must be efficiently detected and then the detected light must be processed with complex computer algorithms to discriminate between normal and cancerous/pre-cancerous cells. There are solutions to the problem in the prior art, most of these using spectroscopy or multispectral imaging. For example, U.S. Pat. No. 6,208,749, which is hereby incorporated by reference in its entirety, utilizes a filter wheel to provide images in at least three spectral bands, analyzes and characterizes each image, where the characteristics are useful in discriminating between normal and cancerous/pre-cancerous cells. The method presented in U.S. Pat. No. 6,208,749 does not obtain images simultaneously and does not provide a method for treatment of pre-cancer or cancerous cells. In U.S. Pat. Nos. 5,115,137 and 4,786,813, both of which are hereby incorporated by reference in their entirety, systems are described that utilize filters to segment the image into four images at separate spectral bands. Since the image is divided by filtering and detection, only a portion of the image is observed in each spectral band. Again, these methods do not provide a means of treatment for pre-cancer or cancerous cells.

In U.S. Pat. No. 6,135,965, Spectroscopic Detection of Cervical Precancer Using Radial Basis Function Networks, also hereby incorporated by reference in its entirety, the fluorescence spectra from a fiber optic fluorimeter at three excitation wavelengths are used to train a neural network for the detection of cervical pre-cancer. The neural network can then be used for detection of cervical pre-cancer. The method of U.S. Pat. No. 6,135,965 is non-imaging, is not coaxial and does not provide a means for treatment of pre-cancer or cancerous cells. In U.S. Pat. No. 6,256,530, also hereby incorporated by reference herein in its entirety, an intensity is measured in a wavelength range and the process repeated to compare intensities of two images at a given wavelength range. This difference is used to differentiate the response of cancerous cells from that of healthy cells. The method of U.S. Pat. No. 6,256,530 is non-imaging and provides a means only for detection, not for treatment of pre-cancer or cancerous cells. In U.S. Pat. No. 5,623,932, also hereby incorporated by reference herein in its entirety, the peak intensities and selected slope measurements of fluorescence spectra are used to differentiate the response of cancerous cells from that of healthy cells. The method in U.S. Pat. No. 5,623,932 for detection is non-imaging and further does not provide a means for treatment of pre-cancer or cancerous cells.

Photodynamic therapy (PDT) is a well-understood method for the treatment of cancerous and pre-cancerous conditions. In this method, a special chemical is introduced to the living tissue. This special chemical is a photo-activated drug that kills surrounding cells when it is activated with a certain wavelength of light. This special chemical is absorbed more by cancerous and pre-cancerous cells than by normal cells. However, normal cells do absorb some of the drug. Prior art descriptions of photo-dynamic therapy involve first injecting the patient with the special drug or applying the agent topically, and then bathing a large, non-descript area of the tissue with activating light. There are several implementations of treatment systems that have introduced elements to restrict or define the illumination area. In U.S. Pat. No. 5,514,127, hereby incorporated by reference in its entirety, a spatial light modulator (SLM) is used to irradiate a selected treatment area. U.S. Pat. No. 5,514,127 requires the use of an endoscope and additionally does not provide treatment simultaneously with detection. In U.S. Pat. No. 6,186,628, also hereby incorporated by reference in its entirety, an acousto-optic modulator (AOM) is used to scan the laser beam in order to customize its shape. The method in U.S. Pat. No. 6,186,628 requires scanning of the treatment beam.

In all of the above systems, the detection and treatment systems are separate and do not interact. Patient comfort, cost containment and health outcomes will be improved by a system in which detection and treatment interact.

It is therefore an object of this invention to detect and locate cancerous and/or pre-cancerous cells in living tissue using a multispectral imager and a comparison of the different-wavelength images and to adaptively and dynamically shape a PDT treatment beam using the images obtained with the multispectral fluorescence imager.

SUMMARY OF THE INVENTION

The object set forth above as well as further and other objects and advantages of the present invention are accomplished by the embodiments of the invention described herein below.

The present invention utilizes a series of optical and electronic elements to detect and image cancerous and/or pre-cancerous cells in living tissue using a multispectral imager. The invention further uses the images thus obtained to shape a Photo-Dynamic Therapy (PDT) light beam so as to maximize the beam's intensity to the areas with the most cancer or pre-cancer and to minimize the amount of normal tissue irradiated by the beam. An illumination source is used to illuminate the tissue sample under investigation. Emitted fluorescent light or reflected light from the tissue sample is collected with an optical system and focused onto a sensor array. Control electronics are used to analyze the images collected on the sensor array. The control electronics determine the intensity map of the illuminated region and the boundaries of any cancerous and/or pre-cancerous cells in the tissue sample under investigation. The control electronics then correspondingly control a treatment light source so that only the areas determined to be cancerous and/or pre-cancerous are illuminated with the treatment light beam, and those areas are illuminated in proportion to the amount of light received from the imager. The treatment light beam is passed through the same optical system used to collect light (through the use of a flip-down mirror or a dichroic beamsplitter) and is thus focused onto the tissue sample. After a pre-determined dose of treatment light is administered, the entire cycle is repeated until the cancerous and/or pre-cancerous cells are diminished below some pre-determined threshold value.

While the present invention can be practiced with a variety of means for obtaining the multispectral image and for detecting the boundaries of the cancerous and/or pre-cancerous cells in the tissue sample under investigation, the preferred embodiment of this invention utilizes a multispectral imager in conjunction with a comparison of the different-wavelength images, to analyze living tissue using fluorescence, autofluorescence, and/or reflectance imaging. The present invention also comprises utilizing spatial information obtained from this tissue analysis to guide the shaping of a treatment beam in a PDT setup.

The present invention improves patient comfort, cost containment and health outcomes by integrating the detection and treatment phases. The treatment light source is spatially-modulated (or beam-shaped) so that only the areas of tissue that are found to be cancerous or pre-cancerous (using the detection method described above) are illuminated with the activation light. The amount of illumination (and its spatial composition) is continuously adapted throughout the treatment. In addition, the treatment and detection systems of this invention are coupled, so that as any cancerous and/or pre-cancerous area is being treated by the treatment system, the area is (either simultaneously or alternately) being detected by the detection system to update not only the boundaries of the diseased region, but the entire area illuminated. As the cancerous or pre-cancerous cells die off, or as the photo-activating agent "bleaches" (non-linearly), the region of tissue that requires illumination will diminish and change shape. This diminishing and shape-changing will be detected by the detection system in real-time or near-real-time, and the shape of the beam and its intensity of activation light will automatically be changed accordingly, so that only the cancerous or pre-cancerous region is being illuminated with activation light and in proportion to the amount of disease.

For a better understanding of the present invention, together with other and further objects thereof, reference is made to the accompanying drawings and detailed description and its scope will be pointed out in the appended claims.

DETAILED DESCRIPTION OF THE INVENTION

In the following descriptions of the present invention, the terms "light", "optical radiation" and "electromagnetic radiation" may be used interchangeably, and these terms both include, but are not limited to, for example, ultraviolet, visible, and near-infrared electromagnetic radiation with wavelength(s) in the range from 0.3 micron to 2 microns. Similarly, the term "optical system", as used herein, includes systems to operate on "electromagnetic radiation", wherein such operations include, but are not limited to, directing, receiving, or filtering "electromagnetic radiation".

While the detailed description of the embodiment of the invention presented hereinbelow is given in relation to detecting and locating any cancerous and/or pre-cancerous cells in the tissue sample, it should be noted that the present invention is capable of detecting, locating and treating abnormalities in a tissue sample where such abnormalities possess optically discernable properties and respond to optical treatment. It should also be noted that a tissue sample as used herein includes living tissue.

Figure 1:
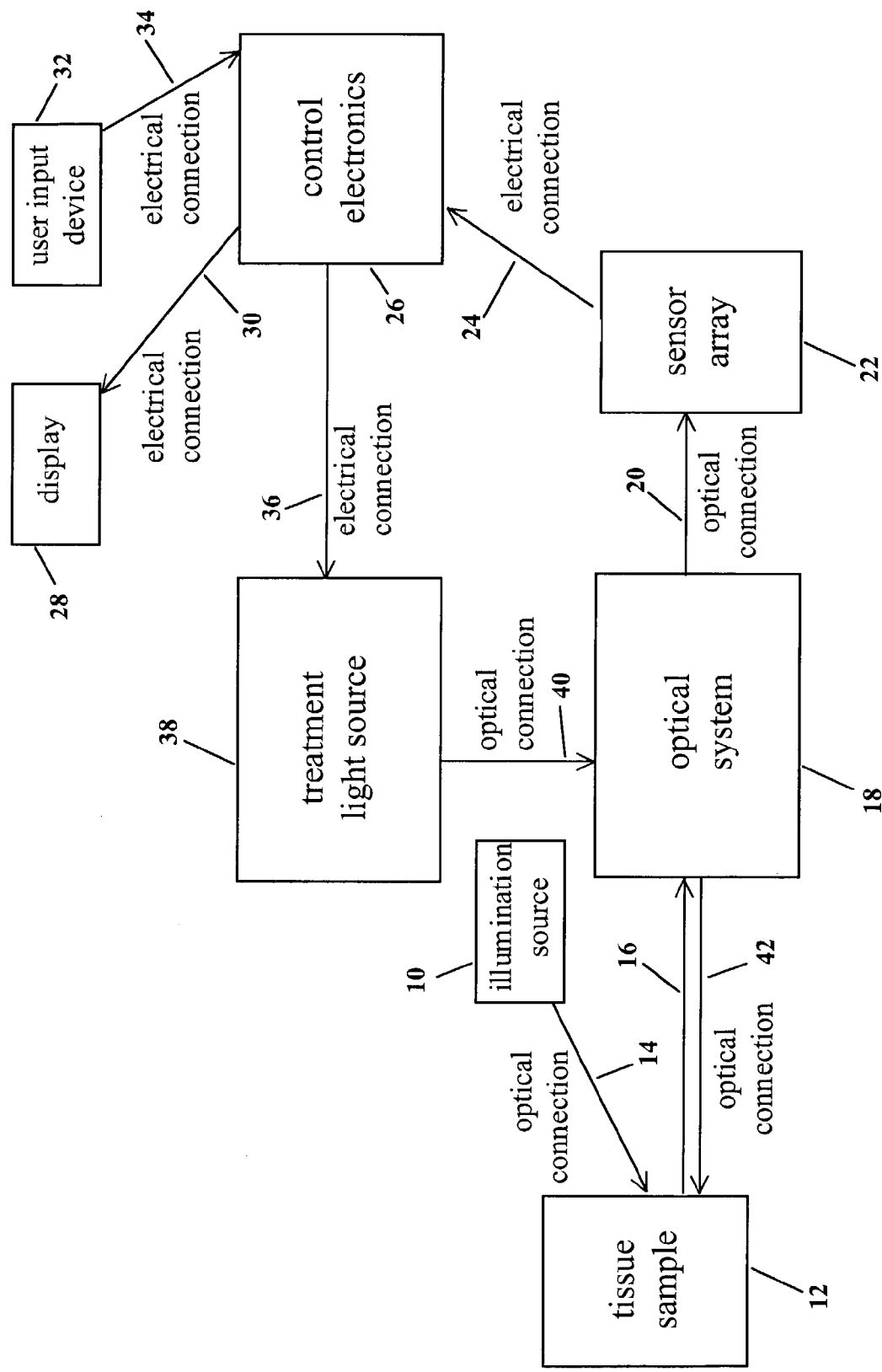
FIG. 1 is schematic illustration of the concept of the invention.

FIG. 1 shows a schematic diagram of the concept of the invention. An illumination source 10 is used to illuminate the tissue sample 12 under investigation with optical radiation 14. Reflected and/or emitted fluorescent optical radiation 16 from the tissue sample 12 is collected with an optical system 18 and the optical radiation is focused 20 onto a sensor array 22. Electronic signals 24 from the sensor array 22 are sent to control electronics 26, which control electronics 26 are used to analyze the images that have been collected on the sensor array 22. The control electronics 26 determine the boundaries of any cancerous and/or pre-cancerous cells in the tissue sample 12 under investigation and map the intensity of the imaged light. A composite image, showing the cancerous and/or pre-cancerous regions overlaid on a color image of the tissue sample is sent from the control electronics 26 to the display 28 via an electrical connection 30. Confirmation of the cancerous and/or pre-cancerous regions in need of treatment is obtained from the user via the user input device 32, which user input device 32 is connected to the control electronics 26 by an electronic connection 34. The user may confirm or deny treatment, and may adjust the locations and shapes of regions to be treated. The control electronics 26 then correspondingly send electronic signals 36 to control a spatially modulated treatment light source 38 so that only the areas determined to be cancerous and/or pre-cancerous are illuminated with the treatment light beam 40 and in proportion to the amount of cancerous and/or pre-cancerous cells found previously. The treatment light beam 40 is passed through the same optical system 18 that was previously used to collect optical radiation 16 from the tissue sample 12 (through the use of a flip-down mirror or a dichroic beamsplitter). The treatment light beam 40, in passing through the optical system 18, is thus focused 42 onto the tissue sample 12. After a predetermined dose of treatment light 42 is administered to the tissue sample 12, the entire cycle is repeated until the cancerous and/or pre-cancerous regions are diminished below some pre-determined threshold size and/or density or until the user determines that the treatment should end.

Figure 2A:
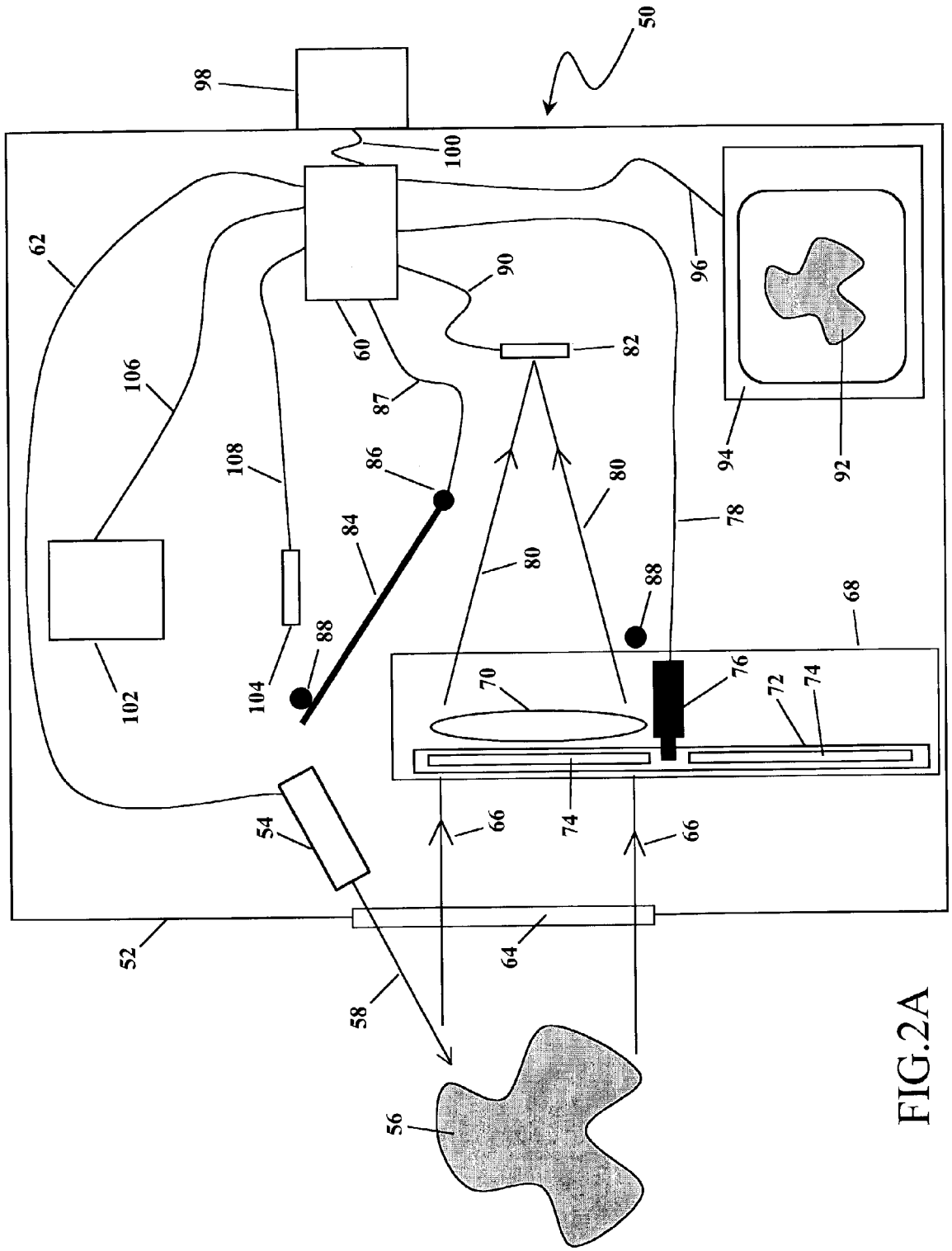
FIG. 2A is a schematic illustration of a first configuration of a first preferred embodiment of the invention.
Figure 2B:
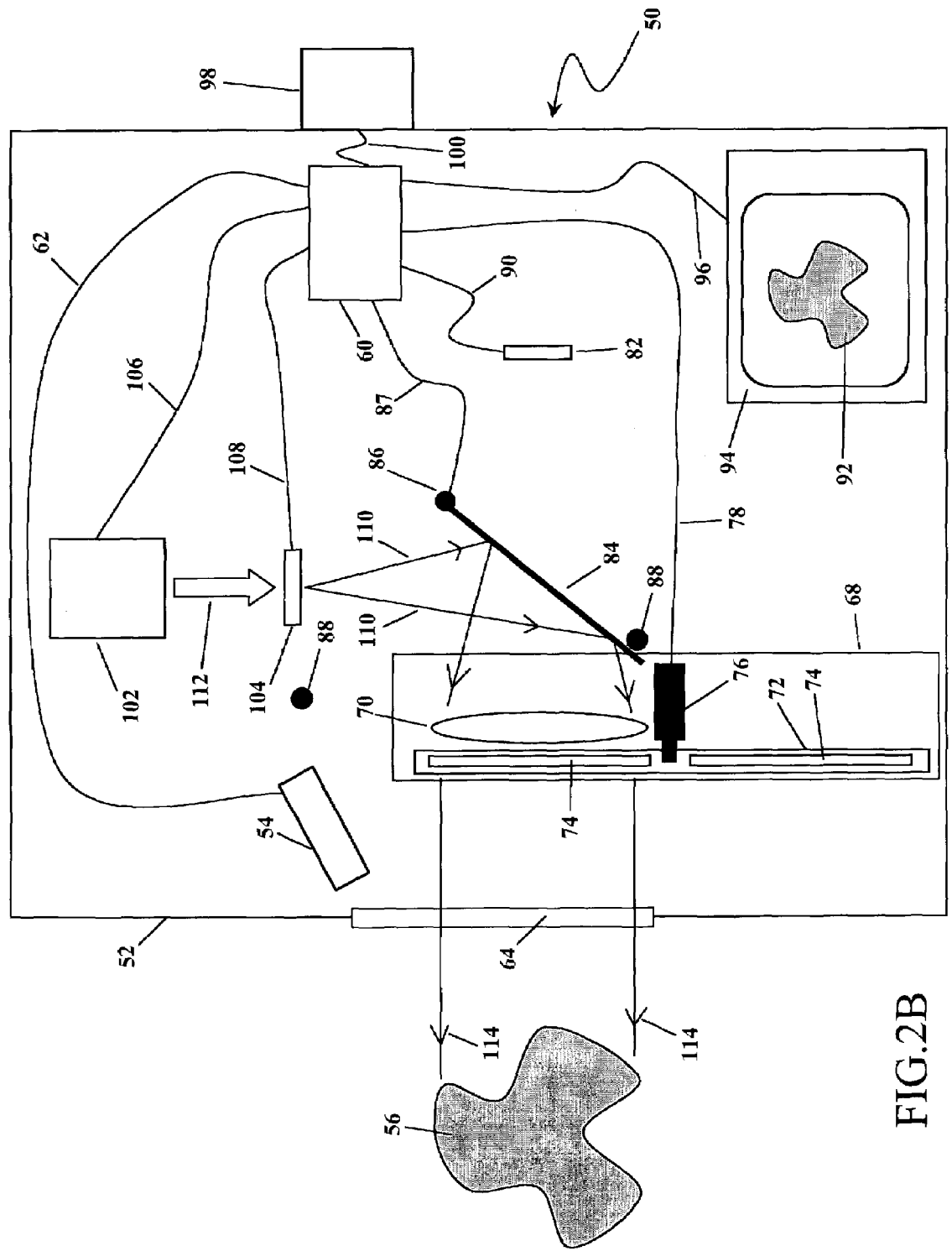
FIG. 2B is a schematic illustration of a second configuration of a first preferred embodiment of the invention.

FIG. 2A and FIG. 2B show schematic illustrations of two configurations of a first preferred embodiment of the invention 50. In FIG. 2A and FIG. 2B, the numbering of the components of the first preferred embodiment of the invention 50 is consistent and only the action of the components differs between the two figures, as will be explained.

The action of this first embodiment of the invention 50 is separated in two distinct phases. The first phase of the action is depicted in FIG. 2A and the second phase of the action is depicted in FIG. 2B.

As shown in FIG. 2A and FIG. 2B, all the components of this embodiment of the invention 50 are enclosed within and/or attached to a housing 52. Referring to FIG. 2A, in the first phase of the action, an illumination source 54 is used to illuminate a target tissue sample 56 with optical radiation 58. The illumination source 54 may emit optical radiation 58 of any range of wavelengths. For example, the illumination source 54 may emit ultraviolet radiation 58 in the range 340-380 nm. Or the illumination source 54 may emit white light 58 in the range 400-700 nm. Or the illumination source 54 may emit infrared radiation 58 in the range 600-900 nm. Or the illumination source 54 may emit a combination of ultraviolet, visible, and/or infrared illumination 58. Furthermore, the various wavelength ranges of the illumination source may be switched on and off and otherwise controlled by the control electronics 60 via electrical wires 62.

Optical radiation 58 from the illumination source 54 is transmitted through a window 64 in the side of the housing 52. Interaction of the optical radiation 58 with the target tissue sample 56 causes reflected and/or fluorescent emitted light 66 to be directed, to some degree, toward and through the window 64. For example, if the illumination source 54 emits ultraviolet radiation 58, then fluorescent light 66 will be emitted from the tissue sample 56. Or if the illumination source 54 emits visible light 58, then visible light 66 will be reflected from the tissue sample 56. Upon passing through the window 64, this reflected and/or fluorescent emitted light 66 is collected with an optical system 68.

Figure 3:
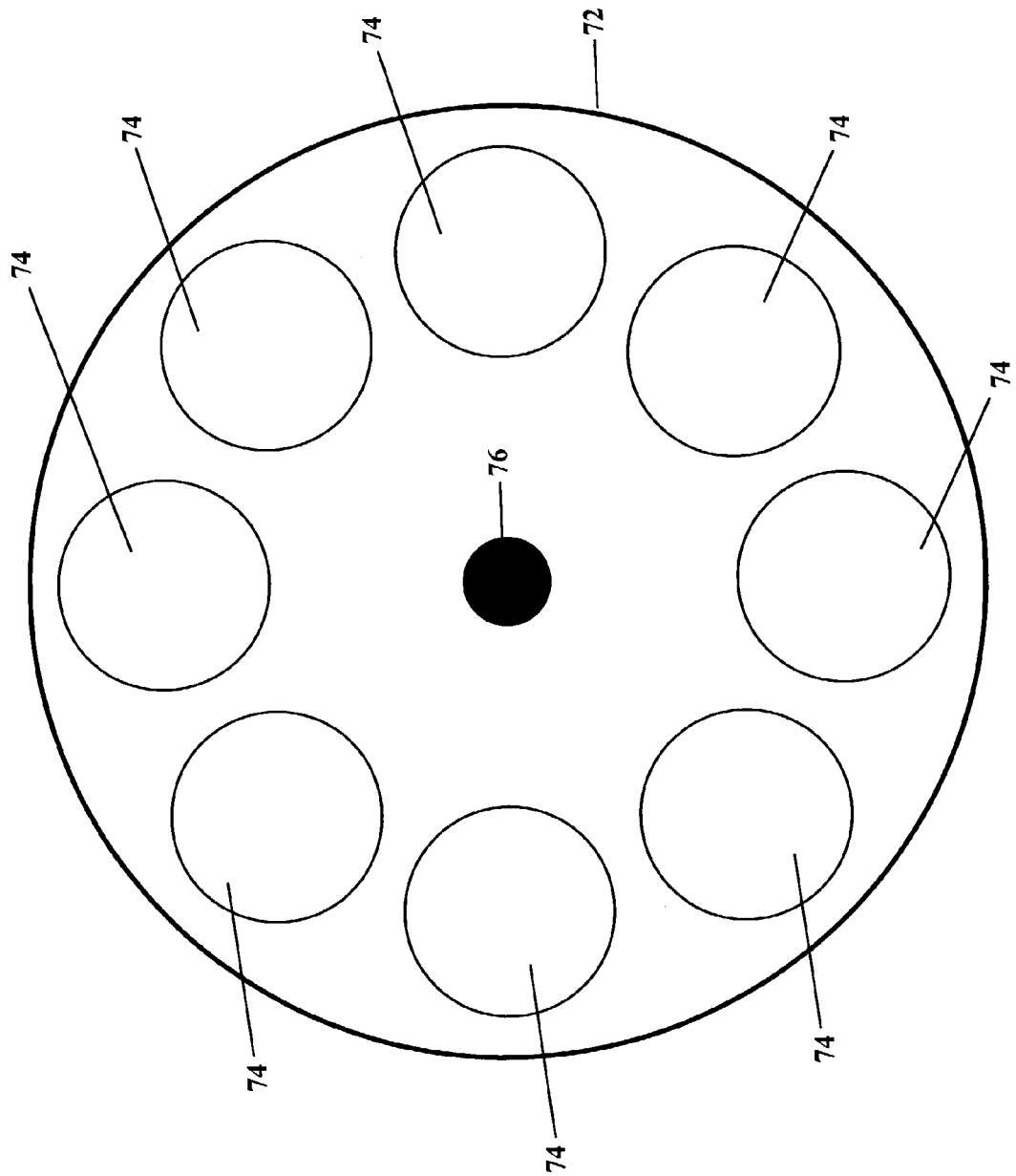
FIG. 3 is a schematic illustration of a filter wheel.

In this first embodiment, the optical system 68 comprises an imaging lens system 70 and a filter wheel 72, which filter wheel 72 itself includes several filters 74, and to which filter wheel 72 is attached a filter wheel drive motor 76. Control of the filter wheel drive motor 76 is maintained via electrical wires 78 connected to the control electronics 60. The filter wheel 72 is fitted with a plurality of filters 74. FIG. 3 shows an example wherein a filter wheel 72 is fitted with eight different filters 74. Each filter 74 may transmit a single, narrow or broad, band of wavelengths, or a certain polarization of light, or a plurality of narrow or broad bands of wavelengths. Referring again to FIG. 2A, with any one filter 74 in place in front of the imaging lens system 70, the optical system 68 causes the incoming reflected and/or fluorescent emitted light 66 to become filtered and subsequently focused 80 onto a sensor array 82. Note that in this first phase of the action, the focused beam 80 passes by a flip-down mirror 84, which flip-down mirror is rotated, via a rotating motor 86, out of the way of the focused beam 80. Action of the rotating motor 86 is controlled by the control electronics 60 via electrical wires 87. Note that the range of motion of the flip-down mirror 84 is bounded by the strategic location of two rubber stop-bumpers 88.

Image information from the sensor array 82 is transmitted to the control electronics 60 via control wires 90. As needed, the control electronics 60 cause the filter wheel 72 to rotate to the next filter 74 in a predetermined series, and the control electronics 60 cause the illumination source 54 to be switched to a different illumination waveband, and image information is again sent from the sensor array 82 to the control electronics 60. After the complete predetermined series of filters 74 and illumination wavebands have been used in this way, the control electronics 60 are used to process the images thus obtained. Mathematical comparison of the various filtered images is used to compute the presence or absence of cancerous and/or pre-cancerous cells in the tissue sample 56. A composite video image 92 is shown on a display screen 94, which composite video image 92 is produced by the control electronics 60 and transmitted to the display screen 94 via electrical wires 96. The composite video image 92 shows the locations, shapes, sizes, and the relative degrees of malignancy of any cancerous and/or pre-cancerous regions overlaid on a visual image of the tissue sample 56.

The user of the invention may interact with the control electronics 60 through the use of a user input device 98, which user input device 98 may consist of one or more of the following: a keyboard, mouse, joystick, or any other common electronic input device. The user input device 98 is connected to the control electronics 60 via a set of electrical wires 100. Through a combination of mathematical comparison of the various filtered images and input from the user, the control (processing/control) electronics 60 determine those regions of the tissue sample 56 that require treatment in the second phase of action. If the control electronics 60 determine that the tissue sample 56 does not require any treatment at this point, then the second phase of action is skipped, and the control electronics 60 surrender control to the user, through the use of the user input device 98.

In the second phase of action, the control electronics 60 exercise control over the remaining components of this first embodiment of the invention 50, namely the treatment optical radiation source 102 and the treatment beam shaping mechanism 104. The treatment light source 102 is connected to the control electronics via electrical wires 106. The treatment beam shaping mechanism 104 is connected to the control electronics via electrical wires 108.

Referring now to FIG. 2B, in the second phase of the action, the control electronics 60 send control signals via electrical wires 62 to the illumination source 54, thereby turning off the illumination source 54. The control electronics 60 next send control signals via electrical wires 87 to the rotating motor 86, thereby moving the flip-down mirror 84 into a position so as to reflect a light treatment beam 110 toward the optical system 68, as shown in FIG. 2B. Note that the range of motion of the flip-down mirror 84 is bounded by the strategic location of two rubber stop-bumpers 88.

The control electronics 60 next send control signals via electrical wires 78 to the filter wheel drive motor 76, thereby causing the filter wheel 72 to turn until a certain, predetermined filter 74 is rotated into place in front of the imaging lens 70 in the optical system 68, which filter 74 is chosen so that it efficiently transmits the treatment light beam 110.

The control electronics 60 next send signals via electrical wires 108 to the treatment beam shaping mechanism 104, thereby ensuring that when the treatment light source 102 is turned on, the shape of the treatment light beam 112 will be properly controlled by spatially-selective transmission through the beam shaping mechanism 104. For example, the treatment beam shaping mechanism 104 may consist of a miniature Liquid Crystal Display (LCD) or Liquid Crystal Light Shutter mechanism, wherein each pixel on the mechanism may be individually turned on or off, thereby allowing or prohibiting light from transmitting through that individual pixel. The pixels of such a device would be turned on and off in such a way that only the regions of the tissue sample 56 that were determined to require light treatment will receive light treatment, and the relative amount of light treatment administered to any given area will be proportional to the amount that was determined to be needed in that area. Because the treatment beam shaping mechanism 104 is intentionally positioned at the a focal plane of the optical system 68, it is a simple matter to turn on the pixels in the treatment beam shaping mechanism 104 that correspond to the pixels in the sensor array 82 that were found to contain images of cancerous and/or pre-cancerous tissue regions.

The control electronics 60 next send signals via electrical wires 106 to the treatment light source 102, thereby turning on the treatment light source 102 and causing treatment light 112 at a certain, predetermined power level and wavelength to be emitted in a direction toward the treatment beam shaping mechanism 104, which treatment beam shaping mechanism 104 causes the treatment light 110 to become shaped so as to act most effectively in the treatment of cancerous and/or pre-cancerous regions of the tissue sample 56. The shaped treatment light 110 next reflects off the flip-down mirror 84 and is thus redirected toward the optical system 68. The imaging lens 70 and filter 74 in the optical system 68 cause the treatment beam 114 to become focused onto the tissue sample 56. Because the treatment beam 114 was previously shaped with the treatment beam shaping mechanism 104, the treatment beam 114 will illuminate only the regions of the tissue sample 56 that have been determined to require illumination with the treatment beam 114. After a pre-determined amount of treatment light 112 has been shone from the treatment light source 102, the control electronics 60 shut off the treatment light source 102. At this point, the control electronics automatically begin the first phase of action once more.

Figure 4:
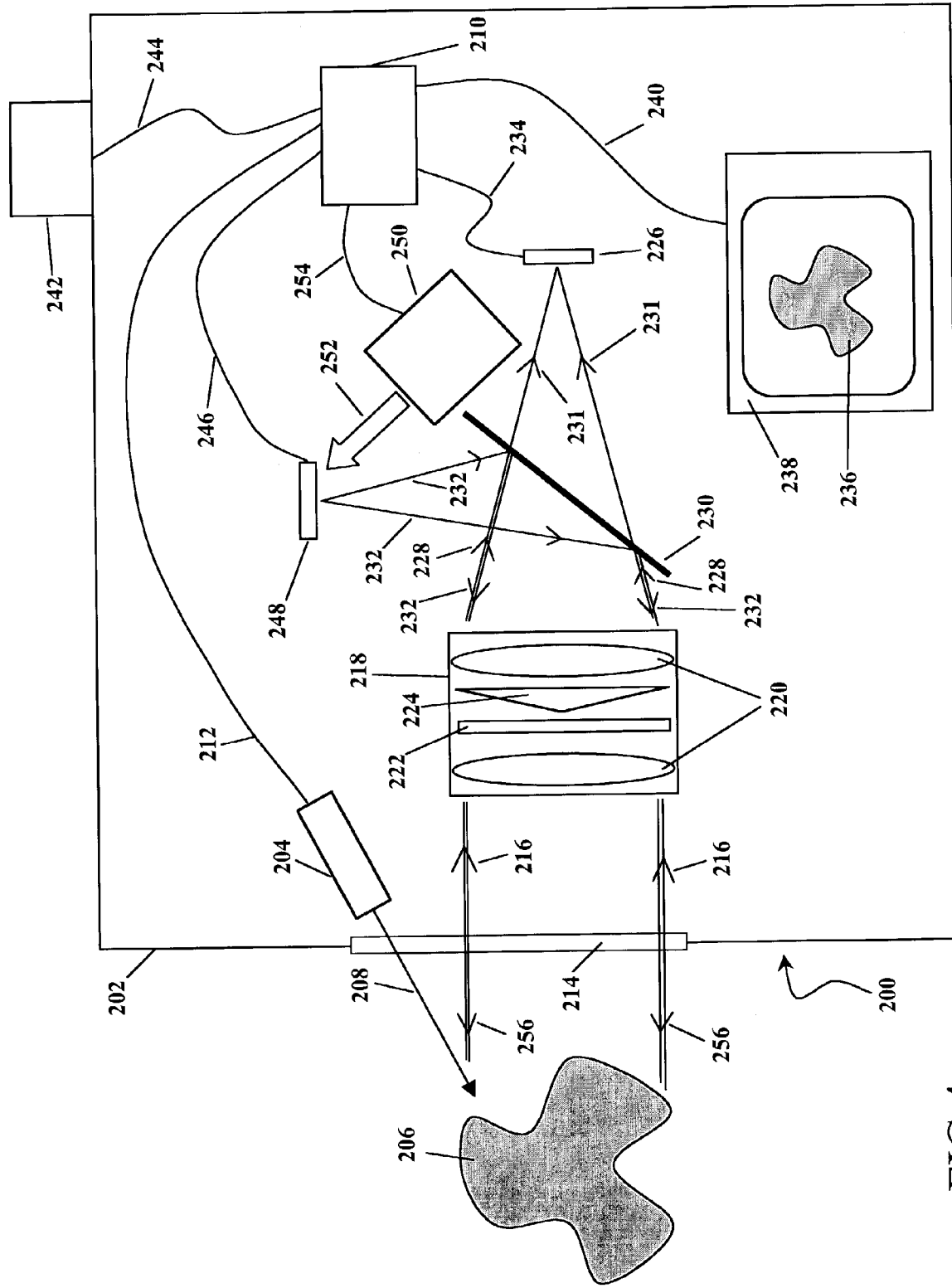
FIG. 4 is a schematic illustration of a second preferred embodiment of the invention.

FIG. 4 shows a schematic illustration of a second preferred embodiment of the invention 200. As shown in FIG. 4, all the components of this embodiment of the invention 200 are enclosed within and/or attached to a housing 202.

First, an illumination source 204 is used to illuminate a target tissue sample 206 with optical radiation 208. The illumination source 204 may emit optical radiation 208 of any range of wavelengths. For example, the illumination source 204 may emit ultraviolet radiation 208 in the range 340-380 nm. Or the illumination source 204 may emit white light 208 in the range 400-700 nm. Or the illumination source 204 may emit infrared radiation 208 in the range 600-900 nm. Or the illumination source 204 may emit a combination of ultraviolet, visible, and/or infrared illumination 208. Furthermore, the various wavelength ranges of the illumination source may be switched on and off and otherwise controlled by the control electronics 210 via electrical wires 212.

Optical radiation 208 from the illumination source 204 is transmitted through a window 214 in the side of the housing 202. Interaction of the optical radiation 208 with the target tissue sample 206 causes reflected and/or fluorescent emitted light 216 to be directed, to some degree, toward and through the window 214. For example, if the illumination source 214 emits ultraviolet radiation 208, then fluorescent light 216 will be emitted from the tissue sample 206. Or if the illumination source 204 emits visible light 208, then visible light 216 will be reflected from the tissue sample 206. Upon passing through the window 214, this reflected and/or fluorescent emitted light 216 is collected with an optical system 218.

In this second embodiment, the multiple imaging optical system 218 comprises a plurality of imaging lens elements 220, a set of filters arranged in a plane 222, and a beam-splitting pyramid prism 224. The exact construction and action of the multiple imaging optical system 218 may, preferably, be as described below.

The multiple imaging optical system uses a series of optical elements to produce multiple simultaneous adjoining images on a single image plane. A first, intermediate, image is produced using the first telecentric imaging lens. This intermediate image is produced at a plane coincident with an adjustable-size rectangular field stop. The rectangular field stop is mounted in a sub-housing that allows its free rotation. A second telecentric lens collimates the light from the intermediate image. This collimated light is next passed through an optical splitting means, which uses the principal of refraction to separate the light into multiple components. The optical splitting means is mounted in a sub-housing that allows its free rotation. From here, the light next passes through a third and final telecentric lens, which produces a second, final, image on a single, planar detection device (such as film or a CCD array). The final image consists of a plurality of identical copies of the intermediate image, each of which may be composed of a different component, or set of components, of the original incident light. The plurality of identical copies of the intermediate image may be arranged such that their edges are adjoining or nearly-adjoining. Size of the multiple identical copies of the intermediate image may be adjusted by adjusting the size of the rectangular field stop. Orientation of the multiple identical copies of the intermediate image may be adjusted by adjusting the rotation of the rectangular field stop. Placement of the multiple identical copies of the intermediate image may be adjusted by adjusting the rotation of the optical splitting means. Further details of the optical system 218 are provided in appendix A of U.S. Provisional Application 60/356,302 and also in U.S. patent application Ser. No. 10/187,912 (filed on Jul. 2, 2002), hereby incorporated by reference.

Figure 5:
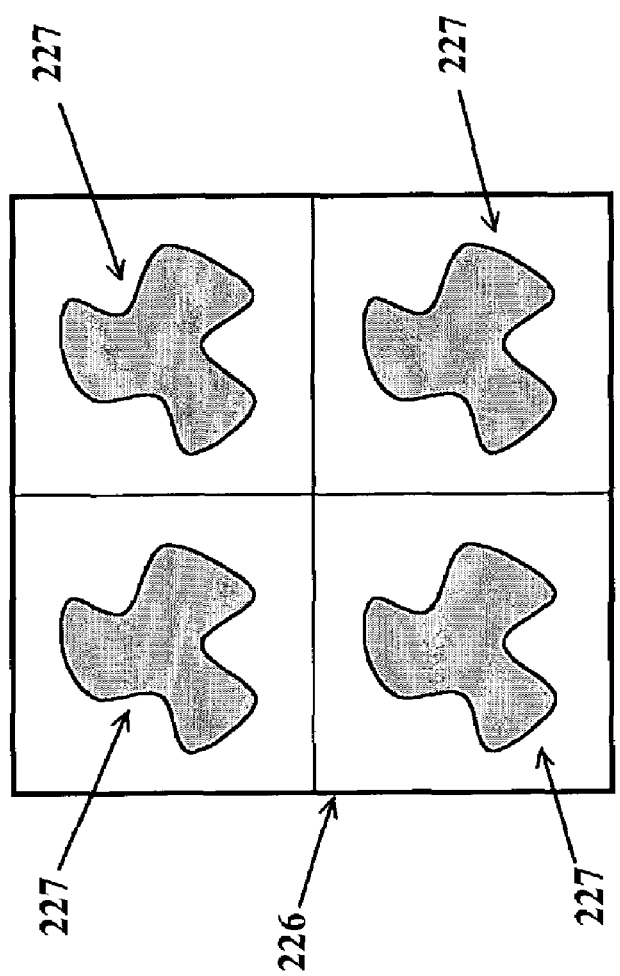
FIG. 5 is a schematic illustration of the concept of a "quad-format" arrangement of images on an image sensor.

The optical system 218 acts to produce a plurality of differently filtered images of the tissue sample 206 on the sensor array 226 simultaneously. Each of the filters in the filter plane 222 may act to transmit a specific band of wavelengths and/or a specific polarization of light. For example, as shown in FIG. 5, four images 227 of the exact same region of the tissue sample 206 may be formed simultaneously on the sensor array 226, arranged so in a so-called "quad-format". Referring again to FIG. 4, the optical system 218 causes the incoming reflected and/or fluorescent emitted light 216 to become filtered and subsequently focused 228 into a plurality of simultaneous images on a sensor array 226, wherein the light forming each of the simultaneous images has passed through a different filter in the filter plane 222. One or more of these filters in the filter plane 222 may be transparent or clear. Also, one or more of these filters in the filter plane 222 may each allow only a single, narrow band of wavelengths of light to pass through. Also, one or more of these filters in the filter plane 222 may each allow only a certain polarization state of light to pass through. Also, one or more of these filters in the filter plane 222 may each allow a plurality of separate bands of wavelengths to pass through. Note that the entire filter plane 222 may be mounted on an easily-replaced fixture, for example a large filter-wheel, allowing either the user or the control electronics to exchange the set of filters in the filter plane 222 with a different set of filters, as may be required at various times in the action of the invention.

The focused light 228 passes through a partial mirror 230 before being transmitted through to the sensor (detector) array 226. Alternately, note that the partial mirror 230 may consist of a flip-down mirror, controlled by the control electronics 210, as explained above in the first embodiment. The partial mirror (controllable transmission component) 230 may allow some or all of the focused image light 228 to pass directly through 229 to the sensor array 226, and may cause some or all of the treatment light 232 to be reflected, as will be explained. For example, the partial mirror 230 may be a dichroic filter 230, which dichroic filter 230 acts to allow light of certain wavelengths to pass through, and light of other wavelengths to be reflected. By using a dichroic filter 230, it is possible to choose a waveband of light for the treatment beam 232 that is different from the band of wavelengths of light 231 that is used to form images on the sensor array 226, thereby maximizing the effect of the dichroic filter 230. Or the partial mirror 230 may be a polarizing beam splitter 230, which polarizing beam splitter 230 acts to allow light of a certain linear polarization to pass through, and light of the perpendicular linear polarization to be reflected. By using a polarizing beam splitter 230, it is possible to choose a polarization of light for the treatment beam 232 that is different from the polarization of light 231 that is used to form images on the sensor array 226, thereby maximizing the effect of the polarizing beam splitter 230.

Image information from the sensor array 226 is transmitted to the control electronics 210 via control wires 234. The control electronics 210 are used to process the images thus obtained. Mathematical comparison of the various filtered images is used to compute the presence or absence of cancerous and/or pre-cancerous cells in the tissue sample 206 and the relative degree of dysplasia (pre-cancer) or cancer. A composite video image 236 is shown on a display screen 238, which composite video image 236 is produced by the control electronics 210 and transmitted to the display screen 238 via electrical wires 240. The composite video image 236 shows the locations, shapes, sizes, and the relative degrees of malignancy of any cancerous and/or pre-cancerous regions overlaid on a visual image of the tissue sample 206.

The user of the invention may interact with the control electronics 210 through the use of a user input device 242, which user input device 242 may consist of one or more of the following: a keyboard, mouse, joystick, or any other common electronic input device. The user input device 242 is connected to the control electronics 210 via a set of electrical wires 244. Through a combination of mathematical comparison of the various filtered images and input from the user, the control electronics 210 determine those regions of the tissue sample 206 that require treatment and in what proportion. If the control electronics 210 determine that the tissue sample 206 does not require any treatment at this point, then the control electronics 210 surrender control to the user, through the use of the user input device 242, and further action of this embodiment of the invention 200 is ceased.

The control electronics 210 next send signals via electrical wires 246 to the treatment beam shaping mechanism 248, thereby ensuring that when the treatment light source 250 is turned on, the shape of the treatment light beam 252 will be properly controlled by spatially-selective reflection from the beam shaping mechanism 248. For example, the treatment beam shaping mechanism 248 may consist of a miniature Digital Light Processor (DLP) or micro-mirror array mechanism, wherein each pixel on the mechanism consists of a tiny micro-mirror, which micro-mirror may be individually turned on or off, thereby allowing or prohibiting a small portion of the treatment light 252 from reflecting in a direction that allows it to be re-imaged with the optical system 218. The pixels of such a device would be turned on and off in such a way that only the regions of the tissue sample 206 that were determined to require light treatment will receive light treatment and in proportion to the intensity map. Because the treatment beam shaping mechanism 248 is intentionally positioned at a focal plane of the optical system 218, it is a simple matter to turn on the pixels in the treatment beam shaping mechanism 248 that correspond to the pixels in the sensor array 226 that were found to contain images of cancerous and/or pre-cancerous tissue regions.

The control electronics 210 next send signals via electrical wires 254 to the treatment light source 250, thereby turning on the treatment light source 250 and causing treatment light 252 at a certain, predetermined power level and wavelength to be emitted in a direction toward the treatment beam shaping mechanism 248, which treatment beam shaping mechanism 248 causes the treatment light 252 to become shaped so as to act most effectively in the treatment of cancerous and/or pre-cancerous regions of the tissue sample 206. The shaped treatment light 232 next reflects off the partial mirror 230 and is thus redirected toward the optical system 218. The imaging lenses 220, the filter plane 222, and the splitting prism 224 in the optical system 218 cause the treatment beam 256 to become focused onto the tissue sample 206. Because the treatment beam 256 was previously shaped with the treatment beam shaping mechanism 248, the treatment beam 256 will illuminate only the regions of the tissue sample 206 that have been determined to require illumination with the treatment beam 256. After a pre-determined amount of treatment light 252 has been shone from the treatment light source 250, the control electronics 210 shut off the treatment light source 250. At this point, the control electronics automatically begin the entire series of action once more.

Figure 6:
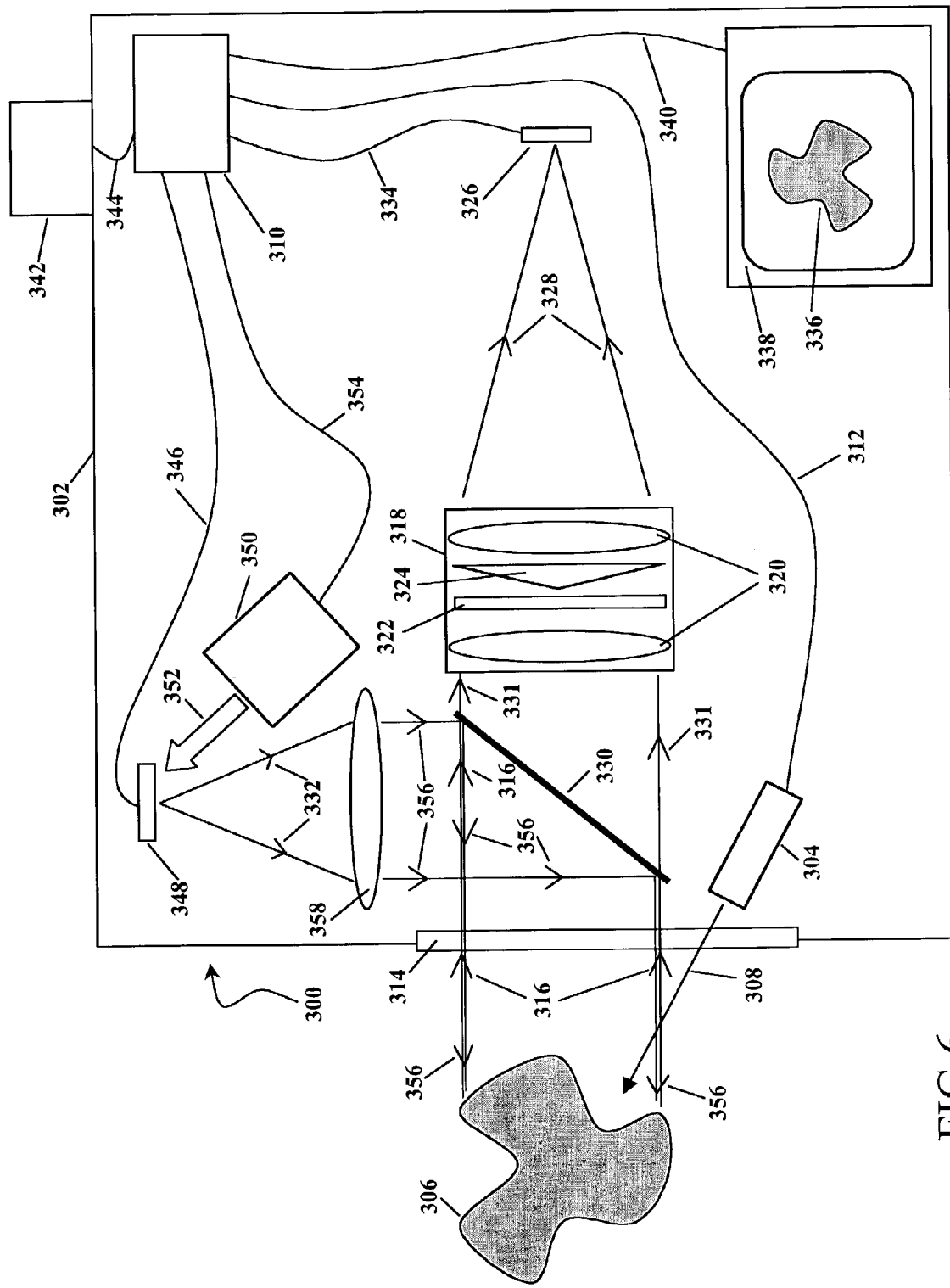
FIG. 6 is a schematic illustration of a third preferred embodiment of the invention.

FIG. 6 shows a schematic illustration of a third preferred embodiment of the invention 300. As shown in FIG. 6, all the components of this embodiment of the invention 300 are enclosed within and/or attached to a housing 302. This third embodiment acts in two separate and distinct phases, which two phases are herein called detection phase and treatment phase. In the normal course of action, the detection phase of action is performed prior to the treatment phase.

In the detection phase of action, an illumination source 304 is used to illuminate a target tissue sample 306 with optical radiation 308. The illumination source 304 may emit optical radiation 308 of any range of wavelengths. For example, the illumination source 304 may emit ultraviolet radiation 308 in the range 340-380 nm. Alternatively, the illumination source 304 may emit white light 308 in the range 400-700 nm. The illumination source 304 may also emit infrared radiation 308 in the range 600-900 nm. Or alternatively, the illumination source 304 may emit a combination of ultraviolet, visible, and/or infrared illumination 308. Furthermore, the various wavelength ranges of the illumination source may be switched on and off and otherwise controlled by the control electronics 310 via electrical wires 312.

Optical radiation 308 from the illumination source 304 is transmitted through a window 314 in the side of the housing 302. Interaction of the optical radiation 308 with the target tissue sample 306 causes reflected and/or fluorescent emitted light 316 to be directed, to some degree, toward and through the window 314. For example, if the illumination source 304 emits ultraviolet radiation 308, then fluorescent light 316 will be emitted from the tissue sample 306. Or if the illumination source 304 emits visible light 308, then visible light 316 will be reflected from the tissue sample 306. Upon passing through the window 314, this reflected and/or fluorescent emitted light 316 is transmitted through the partial mirror 330, and this transmitted light 331 is then collected with an optical system 318.

In this third embodiment, the multiple imaging optical system 318 comprises a plurality of imaging lens elements 320, a set of filters arranged in a plane 322, and a beam-splitting pyramid prism 324. The exact construction and action of the multiple imaging optical system 318 may be substantially the same as that of optical imaging system 218. The optical system 318 acts to produce a plurality of differently filtered images of the tissue sample 306 on the sensor array 326 simultaneously. Each of the filters in the filter plane 322 may act to transmit a specific band of wavelengths or a specific polarization of light. For example, as shown in FIG. 5, four images 227 of the exact same region of the tissue sample 306 may be formed simultaneously on the sensor array 326, arranged in a so-called "quad-format". Referring again to FIG. 6, the optical system 318 causes the incoming reflected and/or fluorescent emitted light 316 to become filtered and subsequently focused 328 into a plurality of simultaneous images on a sensor array 326, wherein the light forming each of the simultaneous images has passed through a different filter in the filter plane 322. One or more of these filters in the filter plane 322 may be transparent or clear. Also, one or more of these filters in the filter plane 322 may each allow only a certain polarization state of light to pass through. Also, one or more of these filters in the filter plane 322 may each allow only a single, narrow band of wavelengths of light to pass through. Also, one or more of these filters in the filter plane 322 may each allow a plurality of separate bands of wavelengths to pass through. Note that the entire filter plane 322 may be mounted on an easily-replaced fixture, such as a filter-wheel, allowing either the user or the control electronics 310 to exchange the set of filters in the filter plane 322 with a different set of filters, as may be required at various times in the action of the invention.

The incoming reflected and/or fluorescent emitted light 316 passes through a partial mirror 330 before being transmitted 331 through to the optical system 318. Note that the partial mirror 330 may consist of a flip-down mirror, controlled by the control electronics 310, as explained above in the first embodiment. Alternatively, the partial mirror 330 may allow some or all of the incoming reflected and/or fluorescent emitted light 316 to pass directly through 331 to the sensor array 326, and may cause some or all of the treatment light 332 to be reflected, as will be explained. For example, the partial mirror 330 may be a dichroic filter 330, which dichroic filter 330 acts to allow light of certain wavelengths to pass through, and light of other wavelengths to be reflected. By using a dichroic filter 330, it is possible to choose a waveband of light for the treatment beam 332 that is different from the band of wavelengths of light 331 that is used to form images on the sensor array 326, thereby maximizing the effect of the dichroic filter 330. Or the partial mirror 330 may be a polarizing beam splitter 330, which polarizing beam splitter 330 acts to allow light of a certain linear polarization to pass through, and light of the perpendicular linear polarization to be reflected. By using a polarizing beam splitter 330, it is possible to choose a polarization of light for the treatment beam 332 that is different from the polarization of light 331 that is used to form images on the sensor array 326, thereby maximizing the effect of the polarizing beam splitter 330.

Image information from the sensor array 326 is transmitted to the control electronics 310 via control wires 334. The control electronics 310 process the images thus obtained. The control electronics 310 use mathematical comparison of the various filtered images to compute the presence or absence of cancerous and/or pre-cancerous cells and the relative degree of dysplasia (pre-cancer) or cancer in the tissue sample 306. A composite video image 336 is shown on a display screen 338, which composite video image 336 is produced by the control electronics 310 and is transmitted to the display screen 338 via electrical wires 340. The composite video image 336 shows the locations, shapes, sizes, and the relative degrees of malignancy of any cancerous and/or pre-cancerous regions overlaid on a visual image of the tissue sample 306.

At this point, control of the treatment procedure may be passed to the user, who would decide whether to continue with treatment of the tissue. If the user decides that treatment is indicated, then the user would initiate the second phase of action of the invention. This second phase of action is called the treatment phase.

The first step of the treatment phase involves the user applying a photosensitizing drug (also called a porphyrin) to the patient. This photosensitizing drug may be applied intravenously or topically. Examples of photosensitizing drugs include Photofrin® and delta- or δ-amino levulinic acid (ALA). The user next allows the drug sufficient time to be absorbed into the cells of the tissue, before the treatment phase continues.

The control electronics 310 send signals via electrical wires 312 to the illumination source 304, thereby causing the tissue sample 306 to be illuminated with white light 308. Reflected light 316 from the tissue sample 306 passes through 331 the partial mirror 330 and enters the optical system 318. The optical system 318 focuses the light 328 onto the sensor array 326. The image information is transferred electronically through an electrical connection 334 from the sensor array 328 to the control electronics 310. This visible reflected image is processed and stored by the control electronics 310. The control electronics 310 shut off the white-light illumination source 304.

At this point, the filter plane 322 in the optical system 318 may be changed by the user or by the control electronics 310, thereby introducing into the filter plane 322 a different set of filters.

The control electronics 310 next send signals via electrical wires 346 to the treatment beam shaping mechanism 348, thereby ensuring that the treatment light beam 352 will be uniformly reflected from the treatment beam shaping mechanism 348.

The control electronics 310 next send signals via electrical wires 354 to the treatment light source 350. The treatment light source is thereby caused to emit low-power light 352 at a certain band of wavelengths such that the photosensitizing drug in the tissue sample 306 will emit fluorescent light 316 but will not be significantly photoactivated. Treatment light 352 from the treatment light source 350 reflects off the treatment beam shaping mechanism 348. This reflected light beam 332 is collimated by the imaging lens 358, and the collimated treatment beam 356 reflects off the partial mirror 330. The collimated treatment beam 356 next passes through the window 314 and is incident upon the tissue sample 306.

Interaction of this low-power treatment beam 356 with the photosensitizing drug in the target tissue sample 306 causes reflected and/or fluorescent emitted light 316 to be directed, to some degree, toward and through the window 314. Upon passing through the window 314, this reflected and/or fluorescent emitted light 316 is transmitted through the partial mirror 330, and this transmitted light 331 is then collected with an optical system 318.

The optical system 318 causes the incoming reflected and/or fluorescent emitted light 331 to become filtered and subsequently focused 328 into a plurality of simultaneous images on a sensor array 326, wherein the light forming each of the simultaneous images has passed through a different filter in the filter plane 322. One or more of these filters in the filter plane 322 may be transparent or clear. Also, one or more of these filters in the filter plane 322 may each allow only a certain polarization state of light to pass through. Also, one or more of these filters in the filter plane 322 may each allow only a single, narrow band of wavelengths of light to pass through. Also, one or more of these filters in the filter plane 322 may each allow a plurality of separate bands of wavelengths to pass through. Note that the entire filter plane 322 may be mounted on an easily-replaced fixture, allowing either the user or the control electronics to exchange the set of filters in the filter plane 322 with a different set of filters, as may be required at various times in the action of the invention.

Image information from the sensor array 326 is transmitted to the control electronics 310 via control wires 334. The control electronics 310 are used to process the images thus obtained. Mathematical comparison of the most-recently captured various filtered images is used to compute the presence or absence of cancerous and/or pre-cancerous cells in the tissue sample 306 and the relative degree of dysplasia (pre-cancer) or cancer. A composite video image 336 is shown on a display screen 338, which composite video image 336 is produced by the control electronics 310 and is transmitted to the display screen 338 via electrical wires 340. The composite video image 336 shows the locations, shapes, sizes, and the relative degrees of malignancy of any cancerous and/or pre-cancerous regions overlaid on a visual (white-light) image of the tissue sample 306. The treatment light source 350 is shut off by the control electronics 310.

At this point, the user of the invention may interact with the control electronics 310 through the use of a user input device 342, which user input device 342 may consist of one or more of the following: a keyboard, mouse, joystick, or any other common electronic input device. The user input device 342 is connected to the control electronics 310 via a set of electrical wires 344. Through a combination of mathematical comparison of the various filtered images and input from the user, the control electronics 310 determine those regions of the tissue sample 306 that require treatment and in what proportion. If the control electronics 310 determine that the tissue sample 306 does not require any treatment at this point, then the control electronics 310 surrender control to the user, through the use of the user input device 342, and further action of this embodiment of the invention 300 is ceased.

The control electronics 310 next send signals via electrical wires 346 to the treatment beam shaping mechanism 348, thereby ensuring that when the treatment light source 350 is turned on, the shape of the treatment light beam 252 will be properly controlled by spatially-selective reflection from the beam shaping mechanism 348. For example, the treatment beam shaping mechanism 348 may consist of a Digital Micromirror Device (DMD), wherein each pixel on the mechanism consists of a tiny micro-mirror, which micro-mirror may be individually turned on or off, thereby allowing or prohibiting a small portion of the treatment light 352 from reflecting in a direction that allows it to be re-imaged with the optical system 358. The pixels of such a device would be turned on and off in such a way that only the regions of the tissue sample 306 that were determined to require light treatment will receive light treatment, and they would receive treatment light 356 in proportion to the amount required. Because the treatment beam shaping mechanism 348 is intentionally positioned at a focal plane of the optical system 358, it is a simple matter to turn on the pixels in the treatment beam shaping mechanism 348 that correspond to the pixels in the sensor array 326 that were found to contain images of cancerous and/or pre-cancerous tissue regions.

The control electronics 310 next send signals via electrical wires 354 to the treatment light source 350, thereby turning on the treatment light source 350 and causing treatment light 352 at a certain, predetermined power level and wavelength to be emitted in a direction toward the treatment beam shaping mechanism 348. The power level and wavelength are determined such that the treatment light beam 356, where it interacts with the tissue sample 306, will cause photoactivation of the photosensitizing drug in the tissue sample 306. The treatment beam shaping mechanism 348 causes the treatment light 352 to become shaped so as to act most effectively in the treatment of cancerous and/or pre-cancerous regions of the tissue sample 306. The shaped treatment light beam 332 is first collimated with the imaging lens 358 and next reflects off the partial mirror 330 and is thus redirected toward the tissue sample 306. The imaging lens 358 causes the treatment beam 332 to become focused, in reflection off the partial mirror 330 onto the tissue sample 306. Because the treatment beam 332 was previously shaped with the treatment beam shaping mechanism 348, the focused treatment beam 356 will illuminate only the regions of the tissue sample 306 that have been determined to require illumination with the treatment beam 356. After a pre-determined amount, or dosage, of treatment light 352 has been shone from the treatment light source 350, the control electronics 310 shut off the treatment light source 350. At this point, the control electronics automatically begin the treatment phase of action once more.

Figure 7:
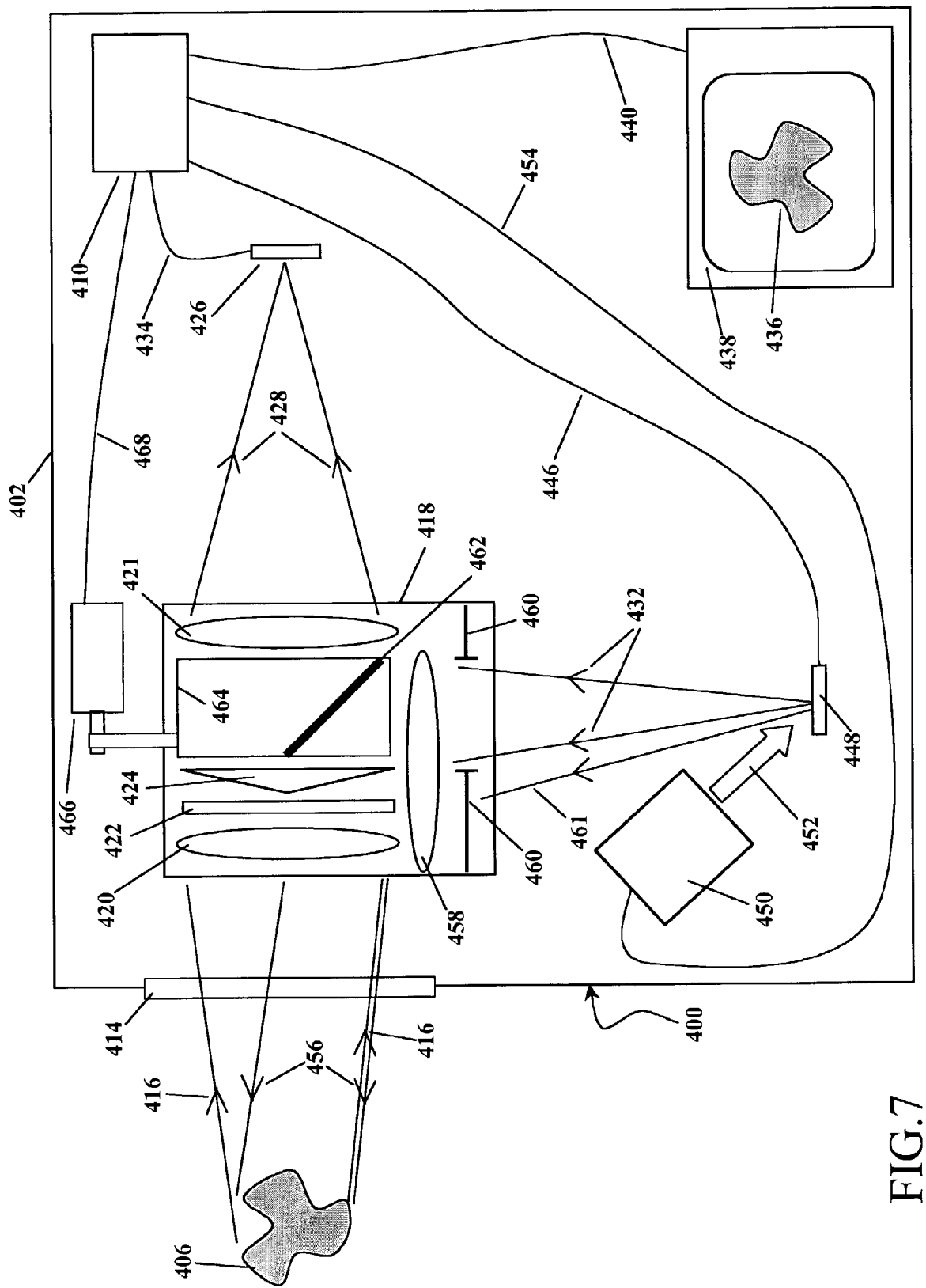
FIG. 7 is a schematic illustration of a fourth preferred embodiment of the invention.

FIG. 7 shows a schematic illustration of a fourth preferred embodiment of the invention 400. As shown in FIG. 7, all the components of this embodiment of the invention 400 are enclosed within and/or attached to a housing 402. This fourth embodiment acts in such a manner that treatment and detection are simultaneous. This fourth embodiment also acts in such a manner that detection and treatment light are coaxial, in that the share a common optical axis through the optical system 418.

In this fourth embodiment, the multispectral imaging system 418 is substantially similar to the multispectral imaging system 218 described in the second embodiment, above. In the current embodiment, however, two elements have been added to the optical system 418. First, a flat reflector 462 is introduced in a position that is substantially near the refracting prism 424. The flat reflector 462 may comprise a full mirror, or a polarizing beamsplitter, or a dichroic reflector, or a partial mirror. The flat reflector 462 is shaped and positioned so that it overlaps with just one quadrant of the prism 424. Second, a lens 458, which lens 458 is substantially similar in design to the original final lens 421, is positioned in a position that is substantially optically conjugate to the position of the original lens 421. Finally, an aperture 460 is added substantially near the lens 458 in order to prevent stray light 461 from entering the optical system 418. The addition of the reflector 462 and the lens 458 and the aperture 460 allows one of the four channels of the multispectral imaging system 418 to be at least partially redirected in a direction away from the imaging sensor plane 426. This one at least partially redirected channel is used in the current embodiment to pass light 432 out through the optical system 418 and toward the target tissue sample 406. With the optical system 418 thus modified from its original conception 218, the current embodiment allows simultaneous detection through at least three of the optical channels and treatment and/or detection through the fourth optical channel.

Note that if the flat reflector 462 is chosen to be a polarizing beamsplitter or a dichroic filter or a partial mirror, then the fourth optical channel will provide an image at the sensor plane 426. In this case, for example, FIG. 5 shows a possible resulting image pattern 226 wherein four images 227 of the exact same region of the tissue sample 406 may be formed simultaneously on the sensor array 426, arranged in a so-called "quad-format". Note that although the four images 227 are shown having identical shapes, each has passed through a separate channel of the optical system 418, and therefore each may have been filtered individually.

Figure 8:
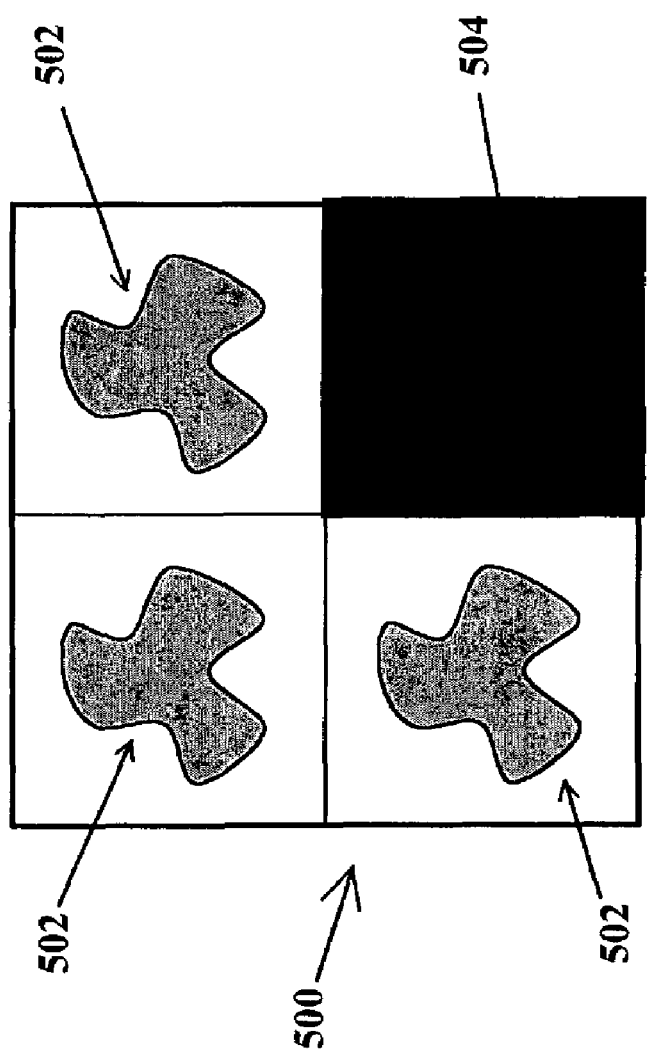
FIG. 8 is a schematic illustration of the concept of a "quad-format" arrangement of three images and one dark region on an image sensor.

Alternatively, for example, if the flat reflector 462 is chosen to be a full mirror, then FIG. 8 shows a possible resulting image 500 received by the sensor plane 426, wherein three copies of the image 502 are produced simultaneously on the sensor plane 426, and the light from one channel, having been redirected by the full mirror 462, is absent, thus leaving one quadrant 504 of the final image 500 completely dark.

Referring again to FIG. 7, note that the flat reflector 462 may be mounted in a moveable housing 464, which housing 464 is designed so as not to optically obstruct any part of the optical path of the imaging system 418. The moveable housing 464 may be easily moved to a position completely outside the optical system 418. The moveable housing 464 may be easily moved either by the user or by a servo control motor 466, which motor 466 is connected via electrical wires 468 to the control electronics 410. When the moveable housing 464 containing the reflector 462 is moved to a position outside the optical system 418, the optical system 418 acts in a manner substantially identical to the manner in which the previously described four-channel multispectral imaging system 218 acts.

The following describes a method of operation of the fourth embodiment, shown in FIG. 7. The first step involves the user applying a photosensitizing drug (also called a porphyrin) to the patient. This photosensitizing drug may be applied intravenously or topically. Examples of photosensitizing drugs include Photofrin® and delta- or δ-amino levulinic acid (ALA). The user next allows the drug sufficient time to be absorbed into the cells of the tissue, before the treatment phase continues.

Control electronics 410 are connected electrically to a light source 450 by electrical wires 454. Signals from the control electronics 410 cause the light source 450 to emit light 452 at a certain, predetermined power level and wavelength range to be emitted in a direction toward the treatment beam shaping mechanism 448. Light 452 from the illumination source 450 impinges upon a spatial light modulator 448 (such as a digital micromirror device, or DMD). As is well understood in the art of DMD systems, the effective reflectivity value of each pixel is controlled by flickering each individual micromirror on and off with a certain duty cycle.

The power level and wavelength range of the emitted light 452 are determined such that the treatment light beam 456, where it interacts with the tissue sample 406, will cause photoactivation of the photosensitizing drug in the tissue sample 406 when the any given pixel in the DMD is set to its highest pixel reflectivity value. The DMD is initially set to act as a plane reflector, with all its pixels in the same effective reflectivity value. Thus at this stage, the level of the reflected light 432 is at a level below that which would cause photoactivation of the photosensitizing drug in the tissue sample 406.

The reflected light 432 passes through an aperture 460, is next focused by a lens 458, and reflects from a reflector 462. The remaining elements 420, 422, 424 of the optical system 418 act to focus the light 456 through the window 414 in the side of the housing 402 and onto the target tissue sample 406. Interaction of the light 456 with the target tissue sample 406 causes reflected and/or fluorescent emitted light 416 to be directed, to some degree, toward and through the window 414. For example, the light 456 may be red, and fluorescent light 416 (at a slightly longer wavelength than the incident light 456) will be emitted from the tissue sample 406. Upon passing through the window 414, this reflected and/or fluorescent emitted light 416 is collected with an optical system 418.

As described previously, the optical system 418 acts to produce a plurality of differently filtered images of the tissue sample 406 on the sensor array 426 simultaneously. In the present example, a four-channel multispectral imaging system 418 produces three simultaneous images on the sensor plane 426, with the fourth channel of the multispectral imaging system 418 being used to transmit light outwards.

Each of the four filters in the filter plane 422 may act to transmit a specific band of wavelengths or a specific polarization of light. For example, three images of the exact same region of the tissue sample 406 may be formed simultaneously on the sensor array 426, arranged in a so-called "quad-format", as shown in FIG. 8, with one of the four image locations being totally devoid of light. Referring again to FIG. 7, the optical system 418 causes the incoming reflected and/or fluorescent emitted light 416 to become filtered and subsequently focused 428 into a plurality of simultaneous images on a sensor array 426, wherein the light forming each of the simultaneous images has passed through a different filter in the filter plane 422. One or more of these filters in the filter plane 422 may be transparent or clear. Also, one or more of these filters in the filter plane 422 may each allow only a certain polarization state of light to pass through. Also, one or more of these filters in the filter plane 422 may each allow only a single, narrow band of wavelengths of light to pass through. Also, one or more of these filters in the filter plane 422 may each allow a plurality of separate bands of wavelengths to pass through. Note that the entire filter plane 422 may be mounted on an easily-replaced fixture, such as a filter-wheel, allowing either the user or the control electronics 410 to exchange the set of filters in the filter plane 422 with a different set of filters, as may be required at various times in the action of the invention. In addition, the flat reflector 462 may be moved into or out of the optical system 418 as described previously.

Image information from the sensor array 426 is transmitted to the control electronics 410 via control wires 434. The control electronics 410 process the images thus obtained. The control electronics 410 use mathematical comparison of the various filtered images to compute the presence or absence of cancerous and/or pre-cancerous cells and the relative degree of dysplasia (pre-cancer) or cancer in the tissue sample 406. A composite video image 436 is shown on a display screen 438, which composite video image 336 is produced by the control electronics 410 and is transmitted to the display screen 438 via electrical wires 440. The composite video image 336 shows the locations, shapes, sizes, and the relative degrees of malignancy of any cancerous and/or pre-cancerous regions overlaid on a visual image of the tissue sample 406.

The control electronics 410 next send signals via electrical wires 446 to the treatment beam shaping mechanism 448, thereby ensuring that the shape of the treatment light beam 452 will be properly controlled by spatially-selective reflection from the beam shaping mechanism 448. For example, the treatment beam shaping mechanism 448 may consist of a miniature Digital Micromirror Device (DMD) wherein each pixel on the mechanism consists of a tiny micro-mirror, which micromirror may be individually turned on or off, thereby allowing or prohibiting a small portion of the treatment light 452 from reflecting in a direction that allows it to be re-imaged with the optical system 418. The pixels of such a device would be turned on and off in such a way that only the regions of the tissue sample 406 that were determined to require light treatment will receive light treatment, and they would receive treatment light 456 in proportion to the amount required. Because the treatment beam shaping mechanism 448 is intentionally positioned at a focal plane of the optical system 418, it is a simple matter to turn on the pixels in the treatment beam shaping mechanism 448 that correspond to the pixels in the sensor array 426 that were found to contain images of cancerous and/or pre-cancerous tissue regions.

The treatment beam shaping mechanism 448 causes the treatment light 452 to become shaped so as to act most effectively in the treatment of cancerous and/or pre-cancerous regions of the tissue sample 406. The shaped treatment light beam 432 is first collimated with the lens 458 and next reflects off the flat reflector 462 and is thus redirected through the remainder of the optical system 418 and then on toward the tissue sample 406. Note that the aperture 460 acts to prevent stray light 461 from entering the imaging system 418. The imaging lens 458 co-acts with the rest of the imaging system 418 to cause the treatment beam 432 to become focused, in reflection off the flat reflector 462 onto the tissue sample 406. Because the treatment beam 432 is shaped with the treatment beam shaping mechanism 448, the focused treatment beam 456 will illuminate with high enough intensity to activate the photoactivated drug only the regions of the tissue sample 406 that have been determined to require treatment. Furthermore, the intensity of the beam at each location on the target tissue sample 406 is also controlled with the treatment beam shaping mechanism 448. While the target tissue sample 406 is being treated with the beam-shaped treatment light 456, the fluorescent and or reflected light 416 from the target tissue sample 406 is simultaneously focused onto the sensor plane 426. The image produced at the sensor plane is used to control the shape of the treatment beam 432 in real-time. Thus, as the photoactivated drug is being activated, the amount of fluorescence and/or reflectance it produces will reduce over time, and the amount of treatment light directed toward it will correspondingly reduce over time. After a pre-determined amount, or dosage, of treatment light 452 has been shone from the treatment light source 450, the control electronics 410 shut off the treatment light source 450.

It should be apparent that the illumination source used in the detection of the cancerous or pre-cancerous cells can be any source that emits in the desired wavelength range. For example, a white light source could be used, a gas discharge lamp could be used as well as a variety of other lamps. It should be noted that the present invention is not limited to these illumination sources. It should also be noted that, in some embodiments, such as, but not limited to, the embodiment shown in FIG. 7, the treatment light source (450 in FIG. 7) is also the detection (illumination) light source.

While several embodiments of methods of collecting the flourescence and reflected signal in several spectral ranges were disclosed (filter wheels and the method of 60/303,243) other methods, such as those of U.S. Pat. No. 5,115,137, U.S. Pat. No. 4,786,813 and U.S. Pat. No. 6,208,749 could be used or adapted to be used.

Although the preferred embodiment of the sensor array 82 or 226 or 326 or 426 is a CCD detector, it should be apparent that a CMOS detector or any optical radiation detector with the appropriate wavelength response could be used.

Although mathematical comparison of the various filtered images is used to compute the presence or absence of cancerous and/or pre-cancerous cells in the tissue sample 56 or 206 or 306 or 406, it should be apparent that other techniques could be used for detection. For example, the method of U.S. Pat. No. 6,135,935 could be used or the method of U.S. Pat. No. 5,623,932 or U.S. Pat. No. 6,256,530 could be adapted and used.

The treatment light source 38, or 102 or 250 or 350 or 450 could be, but is not limited to, a laser emitting light of the appropriate wavelength or a light source such as an LED emitting light of the appropriate wavelength.

The beam shaping mechanism 104 or 248 or 348 or 448 may be, but is not limited to, a spatial light modulator such as a Liquid Crystal array or a Digital Light Processor (such as a Grating Light Valve), a Micro Mirror Array, an Acousto-optic modulator (AOM), or a galvo mirror or an array of galvo mirrors. The beam shaping mechanism 104 or 248 or 348 or 448 may be, in one embodiment, combined with the treatment optical radiation source 102, 250, 350, 450 as, for example, in utilizing a controllable array of sources.

While the embodiments of the present invention has been described above in reference to a treatment beam, it should be noted that "beam" as used hereinabove also refers to more than one beam or a group of "beamlets" as, for example, but not limited to, the resulting radiation formed when a beam is shaped by a Micro Mirror Array or an array of galvo mirrors or produced by a controllable array of sources.

It should also be noted that although the embodiment of the invention described herein below refers to tissue sample, the invention can be practiced in other embodiments where a sample is treated and the treatment detected, such as, but not limited to, the curing of materials or the annealing of materials.

A detailed description of multiple imaging optical system (218, 318, 418) is provided in appendix A of U.S. Provisional Application 60/356,302 and also in U.S. patent application Ser. No. 10/187,912 (filed on Jul. 2, 2002), hereby incorporated by reference. The multiple imaging optical system described in U.S. Provisional Application 60/363,997 can also be used as another embodiment of the multiple imaging optical system of this invention.

Although the invention has been described with respect to various embodiments, it should be realized this invention is also capable of a wide variety, of further and other embodiments.

The invention claimed is:

1. A method for imaging and treating a sample, the method comprising the steps of:
   a) illuminating the sample with electromagnetic radiation from an illumination source;
   b) obtaining a plurality of images from the sample, said plurality of images obtained from illuminating the sample with electromagnetic radiation from the illumination source;
   c) producing a plurality of signals, each signal from said plurality of signals corresponding to one of said plurality of images;
   d) calculating, from at least one signal from said plurality of signals, a location and spatial shape for treatment on the sample;
   e) spatially shaping in substantially real time, using the calculated spatial shape, a treatment electromagnetic radiation beam in order to configure the electromagnetic radiation beam to substantially cover the treatment location;
   f) varying an intensity profile of the treatment electromagnetic radiation beam; and,
   g) illuminating the treatment location with the spatially shaped treatment electromagnetic radiation beam, subsequent to illuminating the sample with electromagnetic radiation from the illumination source, in order to treat the sample;
   said substantially real time spatially shaping the treatment electromagnetic radiation beam precluding scanning the treatment electromagnetic radiation beam.

2. The method of claim 1 further comprising the step of: repeating steps b) through g) automatically until a predetermined condition occurs.

3. The method of claim 1 further comprising the step of: repeating steps (a) through (g) upon user input.

4. The method of claim 1 further comprising the step of: displaying an image of the sample.

5. The method of claim 1 wherein the step of repeating steps b) through g) further comprises the step of:
   repeating steps b) through g) automatically until user input indicates a termination of treatment.

6. The method of claim 1 wherein said treatment electromagnetic radiation beam comprises said illumination beam of electromagnetic radiation.

7. The method of claim 1 wherein the sample is a living tissue sample.

8. The method of claim 1 wherein the step of obtaining a plurality of images from the sample comprises the step of:
   simultaneously obtaining a plurality of images from the sample.

9. The method of claim 1 wherein the step of illuminating the sample with electromagnetic radiation comprises the step of:
   illuminating the sample with an illumination beam of electromagnetic radiation;
   and, wherein the step of illuminating the treatment location with the shaped treatment electromagnetic radiation beam comprises the step of:
   illuminating the treatment location with the shaped treatment electromagnetic radiation beam simultaneously with said illuminating the sample with said illumination beam of electromagnetic radiation.

10. The method of claim 9 wherein the step of illuminating the sample with an illumination beam further comprises the step of:
    illuminating the sample with an illumination beam colinear with an optic axis of an optical system;
    and wherein the step of illuminating the treatment location with the shaped treatment electromagnetic radiation beam further comprises the step of:
    illuminating the treatment location with the shaped treatment electromagnetic radiation beam colinear with said optic axis.

11. The method of claim 1 wherein the step of calculating, from at least one signal from said plurality of signals, said at least one signal comprises at least two signals and the step of calculating comprises the step of:
    comparing at least two signals from said plurality of signals.

12. A system for imaging and treating samples, the system comprising:
    an illumination source of electromagnetic radiation, said illumination source capable of illuminating a sample with electromagnetic radiation;
    an optical sub-system capable of collecting a plurality of images of the sample, said plurality of images resulting from illuminating the sample with electromagnetic radiation from the illumination source, and capable of focusing electromagnetic radiation onto the sample;
    an image detector capable of capturing at least one image from said plurality of images of the sample and producing at least one detector signal;
    a processing/control sub-system capable of calculating location and spatial shape data for at least one location for treatment on the sample, said calculation based on said at least one detector signal; and, a treatment electromagnetic radiation source capable of producing a treatment electromagnetic radiation beam formed to substantially cover said treatment location;

said treatment electromagnetic radiation beam being emitted subsequent to illuminating the sample with electromagnetic radiation from the illumination source; said treatment electromagnetic radiation source comprising:

a treatment beam source;

a treatment beam shaping mechanism capable of shaping, in substantially real time, a treatment beam emanating from said treatment beam source; and said processing/control sub-system also being capable of providing shaping data, said shaping data obtained from calculating location and spatial shape data, and control information to said treatment beam shaping mechanism; said substantially real time spatially shaping the treatment electromagnetic radiation beam precluding scanning the treatment electromagnetic radiation beam;

said optical subsystem being also capable of directing said treatment electromagnetic radiation beam at said at least one treatment location.

13. The system of claim 12 further comprising:
a user input device operably connected to said processing/control sub-system, said user input device being capable of providing information to the processing/control sub-system.

14. The system of claim 12 wherein said optical sub-system includes a controllable transmission component.

15. The system of claim 14 wherein said controllable transmission component comprises a moveable reflective element.

16. The system of claim 15 wherein said processing/control sub-system is also capable of providing control signals for positioning said moveable reflective element.

17. The system of claim 14 wherein said controllable transmission component comprises a filter.

18. The system of claim 14 wherein said controllable transmission component is selected from the group consisting of polarizing beam-splitter, partial mirror and dichroic reflector.

19. The system of claim 12 wherein said processing/control sub-system is also capable of modifying the radiation from said illumination source.

20. The system of claim 12 wherein said optical sub system comprises: at least one filter.

21. The system of claim 12 wherein said treatment beam shaping mechanism comprises a liquid crystal array.

22. The system of claim 12 wherein said treatment beam shaping mechanism comprises a micro-mirror array.

23. The system of claim 12 wherein said treatment beam shaping mechanism comprises an acousto-optic modulator.

24. The system of claim 12 wherein said treatment beam shaping mechanism comprises a digital light processor.

25. The system of claim 12 wherein said treatment beam source comprises said illumination source.

26. The system of claim 12 wherein said processing/control sub-system is also capable of modifying said treatment beam source.

27. The system of claim 26 wherein said modification comprises varying an intensity profile of said treatment beam source.

28. A system for imaging and treating samples, the system comprising:

an illumination source of electromagnetic radiation said illumination source capable of illuminating a sample with electromagnetic radiation;

an optical sub-system capable of collecting a plurality of images of the sample, said plurality of images resulting from illuminating the sample with electromagnetic radiation from the illumination source, and capable of focusing electromagnetic radiation onto the sample;

an image detector capable of capturing at least one image from said plurality of images of the sample and producing at least one detector signal;

a processing/control sub-system capable of calculating location and spatial shape data for at least one location for treatment on the sample, said calculation based on said at least one detector signal; and a treatment electromagnetic radiation source capable of producing a treatment electromagnetic radiation beam formed to substantially cover said treatment location;

said treatment electromagnetic radiation beam being emitted subsequent to illuminating the sample with electromagnetic radiation from the illumination source; said treatment electromagnetic radiation source comprising:

a treatment beam source;

a treatment beam shaping mechanism capable of shaping a treatment beam emanating from said treatment beam source; and said processing/control sub-system also being capable of providing shaping data, said shaping data obtained from calculation location and spatial shape data, and control information to said treatment beam shaping mechanism;

said optical subsystem being also capable of directing said treatment electromagnetic radiation beam at said at least one treatment location; and wherein said optical sub-system comprises:

at least one filter; and wherein said at least one filter comprises at least two filters and said processing/control sub-system is also capable of providing control signals for selecting at least one filter from said at least two filters.

29. The system of claim 28 wherein said optical sub-system is capable of substantially sequentially collecting a plurality of filtered images of sample.

30. A system for imaging and treating samples, the system comprising:

an illumination source of electromagnetic radiation, said illumination source capable of illumination a sample with electromagnetic radiation:

an optical sub-system capable of collecting a plurality of images of the sample, said plurality of images resulting from illuminating the sample with electromagnetic radiation from the illumination source and capable of focusing electromagnetic radiation onto the sample;

an image detector capable of capturing at least one image from said plurality of images of the sample and producing at least one detector signal;

a processing/control sub-system capable of calculating location and spatial shape data for at least one location for treatment on the sample said calculation based on said at least one detector signal; and a treatment electromagnetic radiation source capable of producing a treatment electromagnetic radiation beam formed to substantially cover said treatment location;

said treatment electromagnetic radiation beam being emitted subsequent to illuminating the sample with electromagnetic radiation from the illumination source;
said treatment electromagnetic radiation source comprising:
a treatment beam source;
a treatment beam shaping mechanism capable of shaping a treatment beam emanating from said treatment beam source; and
said processing/control sub-system also being capable of providing shaping data, said shaping data obtained from calculating location and spatial shape data, and control information to said treatment beam shaping mechanism;
said optical subsystem being also capable of directing said treatment electromagnetic radiation beam at said at least one treatment location; and
wherein said optical sub-system comprises:
at least one filter; and
wherein said optical sub-system further comprises an imaging lens component.

31. A system for imaging and treating sample, the system comprising:
an illumination source of electromagnetic radiation said illumination source capable of illuminating a sample with electromagnetic radiation;
an optical sub-system capable of collecting a plurality of images of the sample, said plurality of images resulting from illuminating the sample with electromagnetic radiation from the illumination source and capable of focusing electromagnetic radiation onto the sample;
an image detector capable of capturing at least one image from said plurality of images of the sample and producing at least one detector signal;
a processing/control sub-system capable of calculating location and spatial shape data for at least one location for treatment on the sample said calculation based on said at least one detector signal; and
a treatment electromagnetic radiation source capable of producing a treatment electromagnetic radiation beam formed to substantially cover said treatment location;
said treatment electromagnetic radiation beam being emitted subsequent to illuminating the sample with electromagnetic radiation from the illumination source;
said teamed electromagnetic radiation source comprising;
a treatment beam source;
a treatment beam shaping mechanism capable of shaping a treatment beam emanating from said treatment beam source; and
said processing/control sub-system also begin capable of providing shaping data, said shaping data obtained from calculation location and spatial shape data, and control information to said treatment beam shaping mechanism;
said optical subsystem being also capable of directing said treatment electromagnetic radiation beam at said at least one treatment location;
wherein said optical sub-system comprises:
a plurality of imaging lens elements; and,
a plurality of filters.

32. A system for imaging and treating sample, the system comprising;
an illumination source of electromagnetic radiation said illumination source capable of illuminating a sample with electromagnetic radiation;
an optical sub-system capable of collecting a plurality of images of the sample, said plurality of images resulting from illuminating the sample with electromagnetic radiation from the illumination source and capable of focusing electromagnetic radiation onto the sample;
an image detector capable of capturing at least one image from said plurality of images of the sample and producing at least one detector signal;
a processing/control sub-system capable of calculating location and spatial shape data for at least one location for treatment on the sample said calculation based on said at least one detector signal; and
a treatment electromagnetic radiation source capable of producing a treatment electromagnetic radiation beam formed to substantially cover said treatment location;
said treatment electromagnetic radiation beam being emitted subsequent to illuminating the sample with electromagnetic radiation from the illumination source;
said treatment electromagnetic radiation source comprising;
a treatment beam source;
a treatment beam shaping mechanism capable of shaping a treatment beam emanating from said treatment beam source; and
said processing/control sub-system also being capable of providing shaping data, said shaping data obtained from calculating location and spatial shape data, and control information to said treatment beam shaping mechanism;
said optical subsystem being also capable of directing said treatment electromagnetic radiation beam at said at least one treatment location; and
wherein said optical sub-system comprises:
a plurality of optical filters,
a plurality of imaging lenses, and
a multi-faceted refracting prism.

33. The system of claim 32 wherein said optical sub-system further comprises a dichroic mirror.

34. The system of claim 33 wherein said dichroic mirror is optically disposed between the sample and a remainder of said optical sub-system.

35. The system of claim 33 wherein said dichroic minor is optically disposed between said image detector and a remainder of components of said optical sub-system.

36. The system of claim 32 wherein said optical sub-system further comprises a polarizing beam splitter.

37. The system of claim 36 wherein said polarizing beam splitter is optically disposed between the sample and a remainder of components of said optical sub-system.

38. The system of claim 36 wherein said polarizing beam splitter is optically disposed between said image detector and a remainder of components of said optical sub-system.

39. The system of claim 32 wherein said optical sub-system further comprises an optical reflective element.

40. The system of claim 32 wherein said optical sub-system is capable of substantially simultaneously collecting a plurality of filtered images of the sample.

41. The system of claim 32 wherein said optical sub-system is capable of collecting a plurality of filtered images of the sample and substantially simultaneously focusing electromagnetic radiation onto the sample.

42. A system for imaging and treating samples, the system comprising:
an illumination source of electromagnetic radiation, said illumination source capable of illuminating a sample with electromagnetic radiation:
an optical sub-system capable of collecting a plurality of images of the sample, said plurality of images resulting from illuminating the sample with electromagnetic radiation from the illumination source, and capable of focusing electromagnetic radiation onto the sample;

an image detector capable of capturing at least one image from said plurality of images of the sample and producing at least one detector signal;

a processing/control sub-system capable of calculating location and spatial shape data for at least one location for treatment on the sample, said calculation based on said at least one detector signal; and, a treatment electromagnetic radiation source capable of producing a treatment electromagnetic radiation beam formed to substantially cover said treatment location;

said treatment electromagnetic radiation beam being emitted subsequent to illuminating the sample with electromagnetic radiation from the illumination source;

said treatment electromagnetic radiation source comprising:

a treatment beam source;

a treatment beam shaping mechanism capable of shaping a treatment beam emanating from said treatment beam source; and said processing/control sub-system also being capable of providing shaping data, said shaping data obtained from calculating location and spatial shape data, and control information to said treatment beam shaping mechanism;

said optical subsystem being also capable of directing said treatment electromagnetic radiation beam at said at least treatment location; and wherein said optical sub-system comprises:

a first optical sub-system;

a second optical sub-system;

an aperture stop optically disposed between said first optical sub-system and said second optical sub-system;

said first optical sub-system being capable of directing incoming electromagnetic radiation to a location of said aperture stop;

a beam separating sub-system capable of receiving electromagnetic radiation from said first optical sub-system and separating received electromagnetic radiation into a plurality of beams of electromagnetic radiation, a location of said beam separating sub-system being substantially coincident with the location of said aperture stop; and said second optical sub-system being capable of imaging said plurality of beams of electromagnetic radiation received from said beam separating sub-system into a plurality of images on image plane.

* * * * *

UNITED STATES PATENT AND TRADEMARK OFFICE
CERTIFICATE OF CORRECTION

| | | |
|---|---|---|
| PATENT NO. | : 7,328,060 B2 | Page 1 of 1 |
| APPLICATION NO. | : 10/365012 | |
| DATED | : February 5, 2008 | |
| INVENTOR(S) | : Gregory C. Mooradian et al. | |

It is certified that error appears in the above-identified patent and that said Letters Patent is hereby corrected as shown below:

Claim 28 (col. 22, line 30) should read --calculating-- and not "calculation"
Claim 29 (col. 22, line 45) should read --of the sample-- and not "of sample"
Claim 30 (col. 22, line 49) should read --illuminating-- and not "illumination"
Claim 31 (col. 23, line 20) should read --samples-- and not "sample"
Claim 31 (col. 23, line 49) should read --being-- and not "begin"
Claim 31 (col. 23, line 51) should read --calculating-- and not "calculation"
Claim 35 (col. 24, line 40) should read --mirror-- and not "minor"
Claim 42 (col. 26, line 3) should read --at least one treatment-- and not "at least treatment"

Signed and Sealed this

Twenty-seventh Day of May, 2008

JON W. DUDAS
*Director of the United States Patent and Trademark Office*